US00PP30340P3

(12) United States Plant Patent
van Langen

(10) Patent No.: US PP30,340 P3
(45) Date of Patent: Apr. 2, 2019

(54) ***ECHEVERIA* PLANT NAMED 'TSAECH1606'**

(50) Latin Name: ***Echeveria* hybrid**
Varietal Denomination: TSAECH1606

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 15/932,612

(22) Filed: Mar. 23, 2018

(65) Prior Publication Data

US 2018/0359897 P1 Dec. 13, 2018

(30) Foreign Application Priority Data

Jun. 9, 2017 (QZ) ..... PBR 2017/1237

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Echeveria* hybrid plant named 'TSAECH1606' which is characterized by broad succulent foliage which is lightly concaved and moderately curled upward, light greyed-green juvenile foliage emerging from the center of the rosette, which becomes progressively suffused with greyed-red on the upper and brown on the lower surface moving outward from the center of the rosette, mature foliage at the outermost whorls of the rosette which is moderately suffused with greyed-red on the upper surface and brown on the lower surface, mature foliage which is narrowly margined and tipped pink, as well as the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'TSAECH1606'.

CROSS REFERENCE TO RELATED APPLICATIONS

This application claims priority to the Community Plant Variety Rights application number 2017/1237, filed Jun. 9, 2017, which is herein incorporated by reference.

BACKGROUND OF THE INVENTION

Parentage: 'TSAECH1606' is a hybrid seedling selection resulting from the controlled pollination of an unnamed *Echeveria affinis* plant (not patented), the seed parent, with *Echeveria runyonii* 'Topsy Turvy' (not patented), the pollen parent. The crossing was made by the inventor in the summer of 2014 at a commercial greenhouse in Heerhugowaard, the Netherlands. One seedling resulting from said cross was observed to exhibit unique growth and foliage characteristics and was isolated for further evaluation in order to confirm the distinctness and stability of the characteristics first observed. Upon confirmation of distinctness and stability, 'TSAECH1606' was selected for commercialization in the autumn of 2014.

Asexual Reproduction: Asexual reproduction of the new cultivar 'TSAECH1606', by way of rooting leaf cuttings, was first initiated in the summer of 2015 at the inventor's commercial greenhouse in Heerhugowaard, the Netherlands. Through five subsequent generations, the unique features of this cultivar have proven to be stable and true to type.

SUMMARY OF THE INVENTION

The cultivar 'TSAECH1606' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1606'. These characteristics in combination distinguish 'TSAECH1606' as a new and distinct *Echeveria* hybrid cultivar:

1. 'TSAECH1606' exhibits succulent foliage arranged in a basal rosette; and
2. 'TSAECH1606' exhibits broad spatulate to obovate foliage which is lightly concaved and moderately curled upward; and
3. 'TSAECH1606' exhibits light greyed-green juvenile foliage emerging from the center of the rosette, which is suffused with brown on the lower leaf surface and tipped with pink; and
4. 'TSAECH1606' exhibits foliage which becomes progressively suffused with greyed-red on the upper surface and brown on the lower surface, moving outward from the center of the rosette; and
5. 'TSAECH1606' exhibits mature foliage at the outermost whorls of the rosette which is moderately suffused with greyed-red on the upper surface and brown on the lower surface, and narrowly margined and tipped pink.

BOTANICAL DESCRIPTION OF THE PLANT

Figure 1:
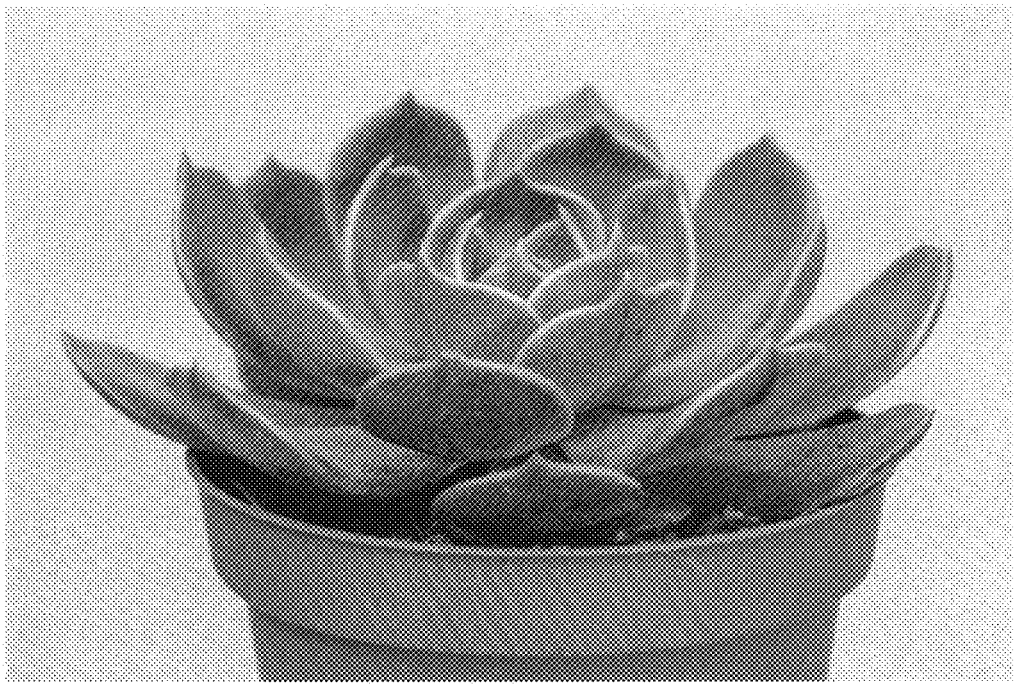
FIG. 1 illustrates, as nearly true as it is reasonably possible to make the same in color photographs of this type, an exemplary plant of 'TSAECH1606' grown in a commercial greenhouse in Heerhugowaard, the Netherlands. This plant is approximately 6 months old, shown planted in a 10 cm container.
Figure 2:
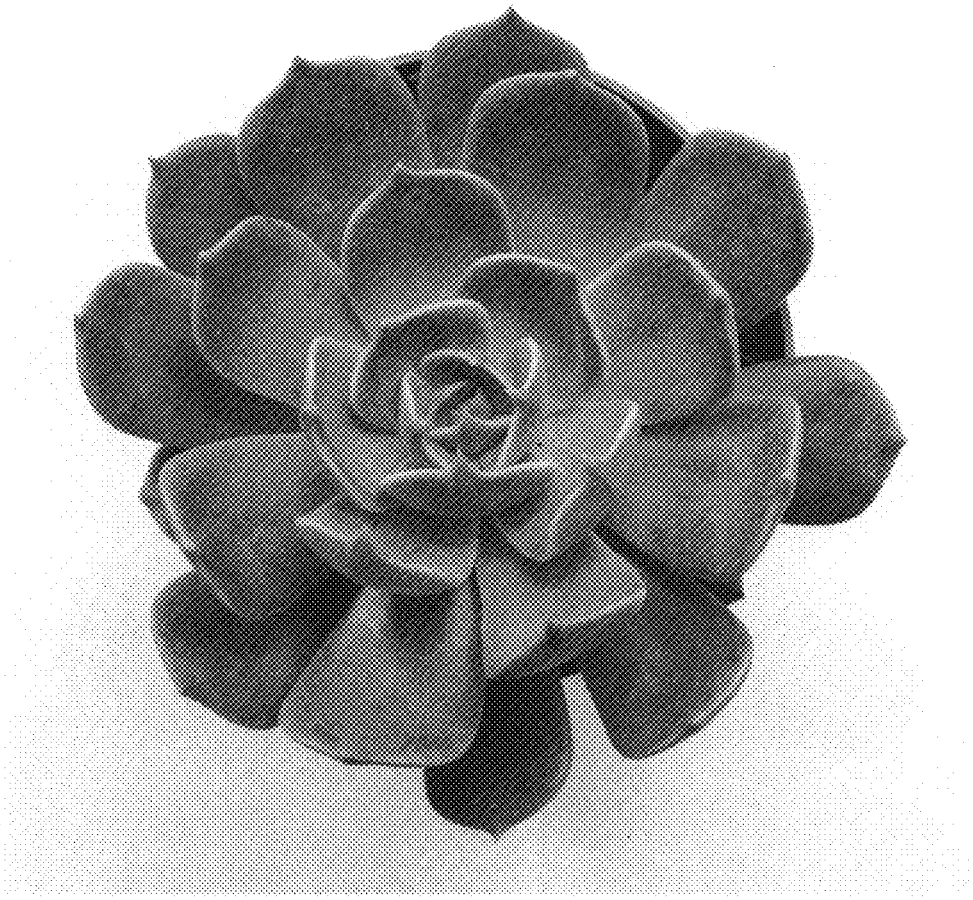
FIG. 2 illustrates, as nearly true as it is reasonably possible to make the same in color photographs of this type, the typical foliage arrangement of 'TSAECH1606'.
Figure 3:
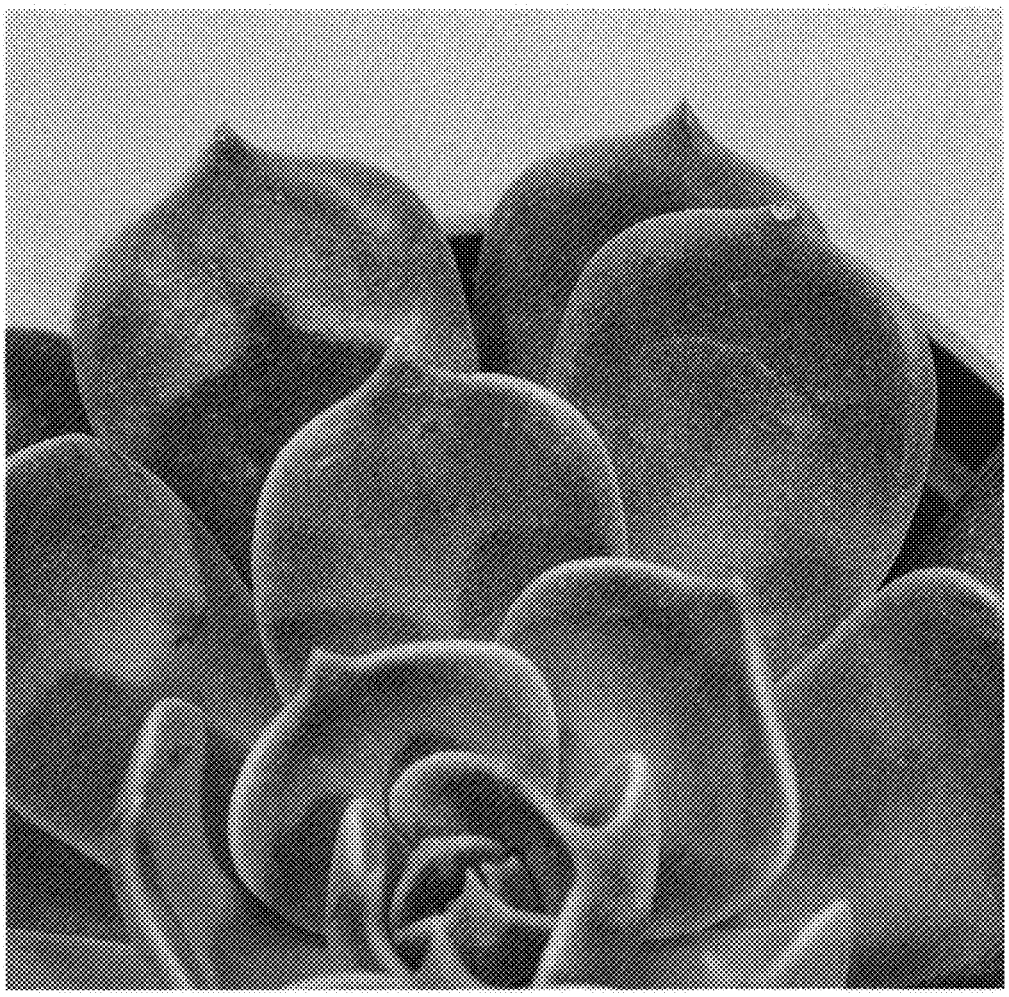
FIG. 3 illustrates, as nearly true as it is reasonably possible to make the same in color photographs of this type, the adaxial surface of the mature foliage 'TSAECH1606'.
Figure 4:
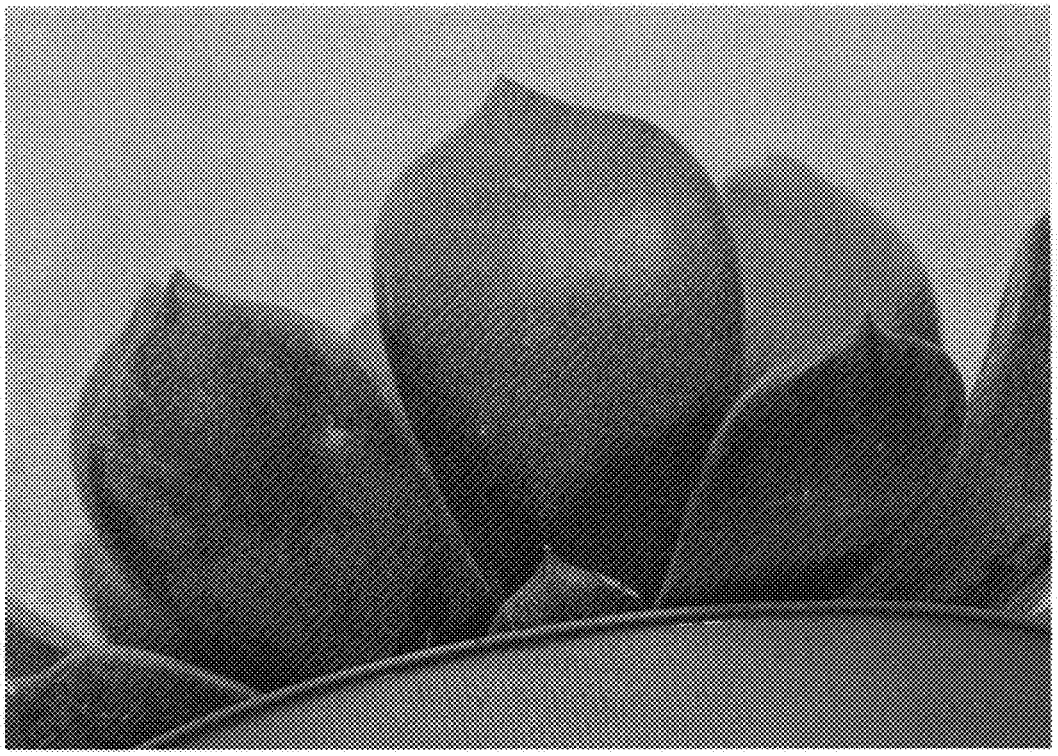
FIG. 4 illustrates, as nearly true as it is reasonably possible to make the same in color photographs of this type, the abaxial surface of the mature foliage 'TSAECH1606'.

The following observations and measurements made in January of 2018 describe averages from a sample set of six specimens of 6 months old 'TSAECH1606' plants grown in 10 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1606' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1606' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—5.9 cm.

*Plant spread.*—Average of 13.0 cm.

*Growth rate.*—Moderate.

*Plant vigor.*—Moderate.

*Propagation.*—Type — Leaf cuttings. Time to initiate rooting — Approximately 21 days at 18 degrees Celsius. Crop time — Approximately 35 weeks to produce a marketable plant in a 10 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 29 leaves per rosette.

*Shape.*—Thick, succulent leaves which are broad spatulate to obovate.

*Dimensions.*—6.1 cm long, 2.85 cm wide, and 0.5 cm thick, on average.

*Aspect.*—Slightly concave and moderately curved upward.

*Attitude.*—Younger foliage near the center of the rosette is very upright; foliage becoming progressively more relaxed towards the outer whorl of the rosette yet still generally upright; average angle of 45 degrees from horizontal.

*Apex.*—Apiculate.

*Base.*—Cuneate.

*Margin.*—Entire; not undulated or lobed.

*Pubescence, texture and luster of the adaxial surface.*—Glabrous, smooth, and matte; moderately glaucous.

*Pubescence, texture and luster of the abaxial surface.*—Glabrous, smooth, and matte; moderately glaucous.

*Color.*—Juvenile foliage, adaxial surface — Yellow-green, nearest to RHS 148B; fading to greyed-green towards the base, nearest to a combination of RHS 193B and 193C; fading to a mixture of yellow-green and greyed-green towards the apex, RHS 148A and 197B; narrowly margined green-white, nearest to a mixture of RHS 157C and 157D; the epicuticular glaucous wax covering the leaf surface is greyed-green, nearest to RHS 198A. Juvenile foliage, abaxial surface — Greyed-green, nearest to RHS 191B; fading to a lighter shade of greyed-green towards the base, nearest to a mixture of RHS 193A and 193B; fading to a darker shade of greyed-green towards the apex, nearest to a mixture of RHS 197A and 197B; narrowly margined green-white, nearest to a mixture of RHS 157C and 157D; the epicuticular glaucous wax covering the leaf surface is greyed-green, nearest to RHS 198A. Mature foliage, adaxial surface — Yellow-green, nearest to RHS 148A; fading to greyed-green towards the base, nearest to a combination of RHS 195A and 195B; suffused with greyed-red towards the apex, RHS 178A; tipped and narrowly margined greyed-red towards the apex, nearest to RHS 180B; the epicuticular glaucous wax covering the leaf surface is greyed-green, nearest to RHS 198A. Mature foliage, abaxial surface — Greyed-green, nearest to RHS 197A; fading to greyed-green, nearest to RHS 194B, towards the base; tipped and narrowly margined greyed-red towards the apex, nearest to RHS 180B;

the epicuticular glaucous wax covering the leaf surface is greyed-green, nearest to RHS 198A.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1606' differ from the seed parent, an unnamed *Echeveria affinis* plant (not patented), in the following characteristics described in Table 1 below.

TABLE 1

| Characteristic | 'TSAECH1606' | *Echeveria affinis* seed parent. |
|---|---|---|
| Plant size. | Larger than the seed parent. | Smaller than 'TSAECH1606'. |
| Foliage width. | Narrower than the seed parent. | Wider than 'TSAECH1606'. |
| General coloration of the foliage. | Yellow-green and lightly to moderately suffused with brown; mature foliage is margined light pink. | Yellow-green and heavily suffused with black; mature foliage is margined red. |

Plants of the new cultivar 'TSAECH1606' differ from the pollen parent, *Echeveria runyonii* 'Topsy Turvy' (not patented), in the following characteristics described in Table 2 below.

TABLE 2

| Characteristic | 'TSAECH1606' | 'Topsy Turvy' |
|---|---|---|
| Foliage aspect. | Slightly concaved. | Strongly revolute or inversely keeled. |
| General coloration of the foliage. | Yellow-green and lightly to moderately suffused with brown; mature foliage is margined light pink. | Blue-gray. |

COMPARISONS WITH THE CLOSEST KNOWN COMPARATOR

Plants of the new cultivar 'TSAECH1606' differ from the closest known commercial comparator, *Echeveria* sp. 'Echoc' (not patented), in the following characteristics described in Table 3 below.

TABLE 3

| Characteristic | 'TSAECH1606' | 'Echoc' |
|---|---|---|
| Plant size. | Larger than 'Echoc'. | Smaller than 'TSAECH1606'. |
| General coloration of the foliage. | Yellow-green and lightly to moderately suffused with brown; mature foliage is margined light pink. | Yellow-green and heavily suffused with a mixture of greyed-purple, red and brown. |
| Foliage luster. | Less glossy. | More glossy. |

That which is claimed is:

1. A new and distinct variety of *Echeveria* hybrid plant named 'TSAECH1606', substantially as described and illustrated herein.

* * * * *